(12) United States Patent
Baker et al.

(10) Patent No.: US 11,610,510 B2
(45) Date of Patent: Mar. 21, 2023

(54) METERED DOSE INHALER TRAINING DEVICE

(71) Applicant: NOBLE INTERNATIONAL, INC., Orlando, FL (US)

(72) Inventors: Jeff Baker, Orlando, FL (US); Christopher Wai Yin Chung, Orlando, FL (US); Francis Michael Siemer, Orlando, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 1196 days.

(21) Appl. No.: 16/093,402

(22) PCT Filed: Apr. 12, 2016

(86) PCT No.: PCT/US2016/027107
§ 371 (c)(1),
(2) Date: Oct. 12, 2018

(87) PCT Pub. No.: WO2017/180107
PCT Pub. Date: Oct. 19, 2017

(65) Prior Publication Data
US 2019/0130790 A1    May 2, 2019

(51) Int. Cl.
*G09B 23/28*    (2006.01)
*A61M 15/00*    (2006.01)
(Continued)

(52) U.S. Cl.
CPC .............. *G09B 23/28* (2013.01); *A61K 9/008* (2013.01); *A61M 15/009* (2013.01);
(Continued)

(58) Field of Classification Search
CPC . G09B 23/28; G09B 5/02; G09B 5/04; G09B 19/24; A61K 9/008; A61M 15/0013; A61M 15/009; A61M 15/0095
(Continued)

(56) References Cited

U.S. PATENT DOCUMENTS 5,363,842 A    11/1994    Mishelevich et al.
5,724,986 A    3/1998    Jones, Jr. et al.
(Continued)

FOREIGN PATENT DOCUMENTS

WO    2016030521 A1    3/2016

OTHER PUBLICATIONS

PCT/US2016/027107; International Search Report and Written Opinion, dated Dec. 8, 2016, 14 pages.
EP16898796 Search Report; dated Oct. 25, 2019; 8 pages.

*Primary Examiner* — Tai T Nguyen
(74) *Attorney, Agent, or Firm* — Timothy H. Van Dyke; Wolter, Van Dyke, Davis, PLLC

(57) ABSTRACT

In an embodiment, a metered dose inhaler (MDI) training device is provided herein. The MDI training device may include a housing having an inhalation port, an opening for receiving ambient air, the inhalation port and the opening are fluidly connected to provide an air flow channel, and a valve associated with the air flow channel, the valve having an opened state and a closed state, and an actuation member, wherein the valve is not allowed to enter the opened state if the actuation member is actuated prior to inhalation through the inhalation port.

19 Claims, 8 Drawing Sheets

(51) Int. Cl.
*G09B 19/24* (2006.01)
*A61K 9/00* (2006.01)
*G09B 5/02* (2006.01)
*G09B 5/04* (2006.01)

(52) U.S. Cl.
CPC .... *A61M 15/0013* (2014.02); *A61M 15/0095* (2014.02); *G09B 5/02* (2013.01); *G09B 5/04* (2013.01); *G09B 19/24* (2013.01); *A61M 2205/581* (2013.01); *A61M 2205/583* (2013.01); *A61M 2205/587* (2013.01); *A61M 2209/02* (2013.01)

(58) Field of Classification Search
USPC ....................................................... 434/262
See application file for complete search history.

(56) References Cited

U.S. PATENT DOCUMENTS

| | | | |
|---|---|---|---|
| 5,758,638 A | 6/1998 | Kreamer | |
| 6,422,234 B1 | 7/2002 | Bacon | |
| 2005/0161467 A1* | 7/2005 | Jones | A61M 15/009 222/23 |
| 2006/0037611 A1 | 2/2006 | Mahon | |
| 2007/0227535 A1* | 10/2007 | Harrington | B05B 7/00 239/338 |
| 2013/0008436 A1* | 1/2013 | Von Hollen | A61M 15/009 128/200.14 |
| 2016/0049096 A1 | 2/2016 | Bruin et al. | |
| 2016/0325058 A1* | 11/2016 | Samson | A61B 5/0022 |

\* cited by examiner

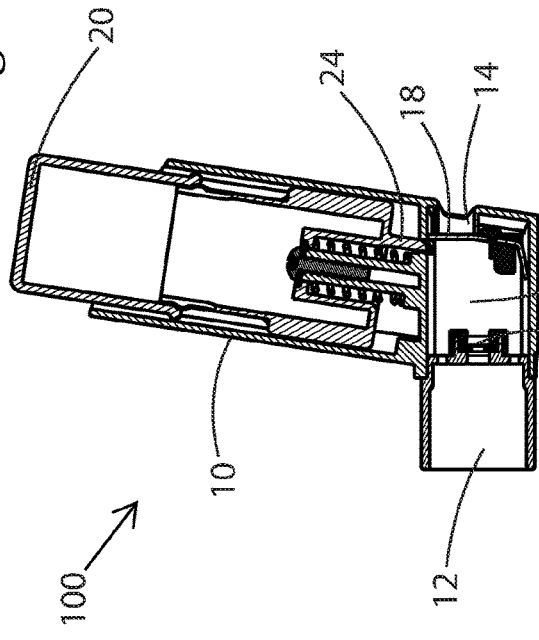
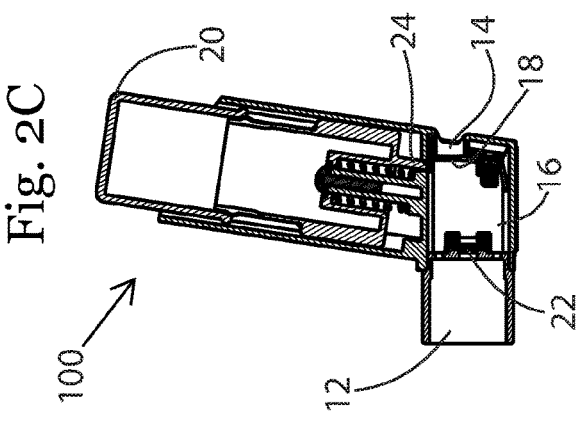
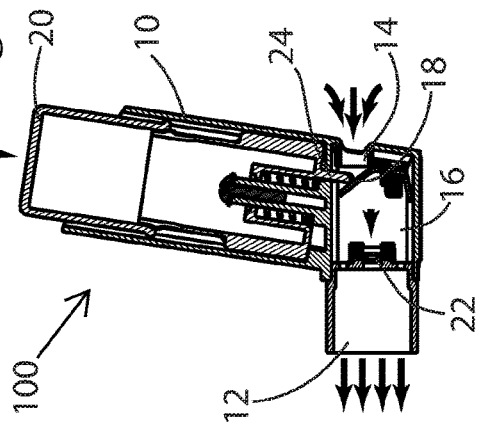
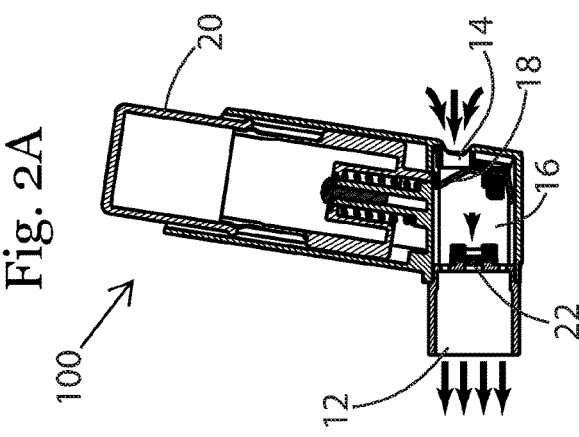

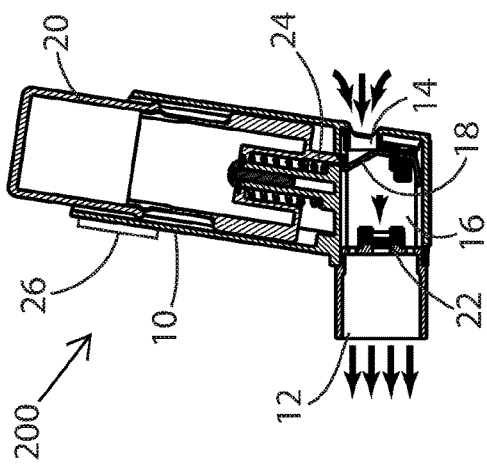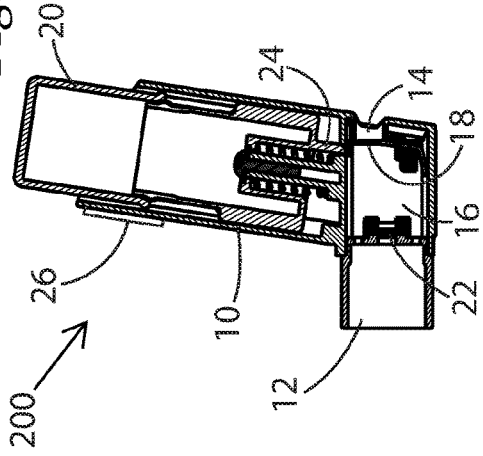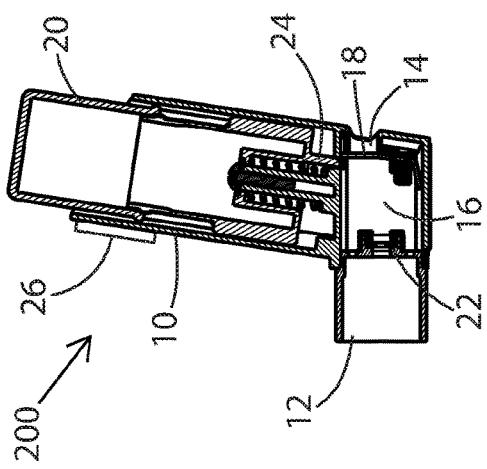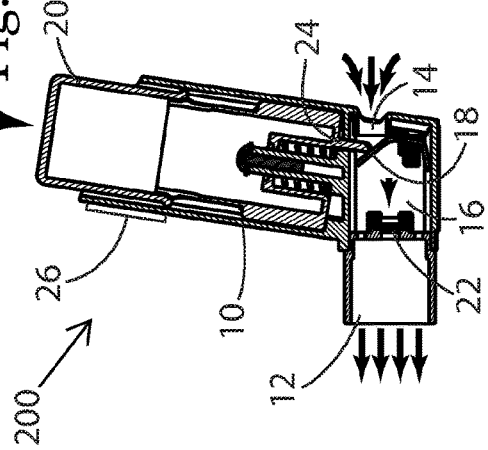

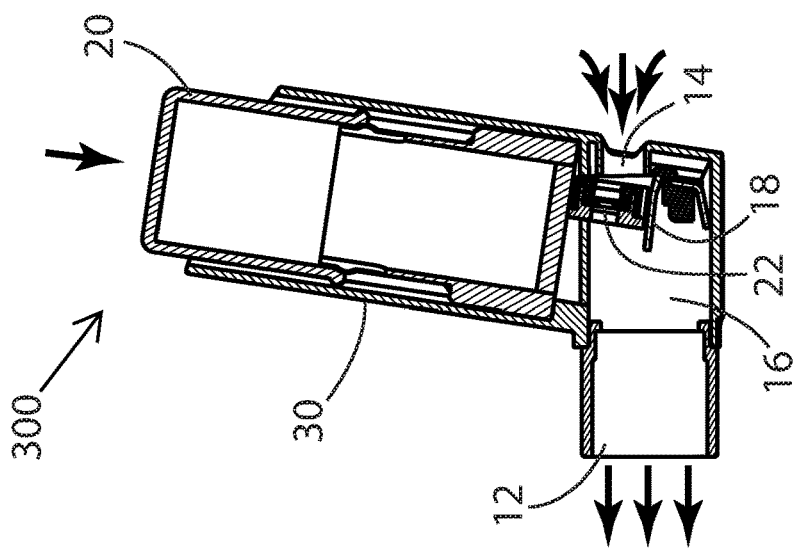
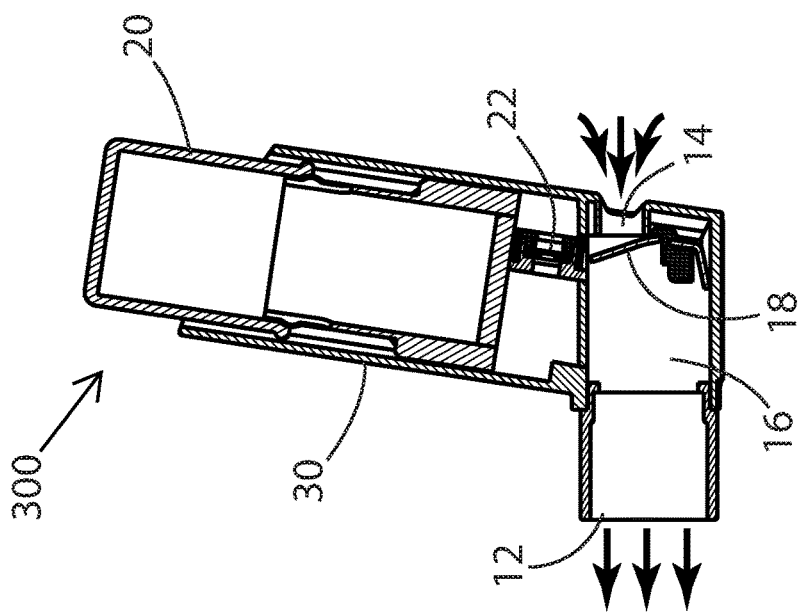
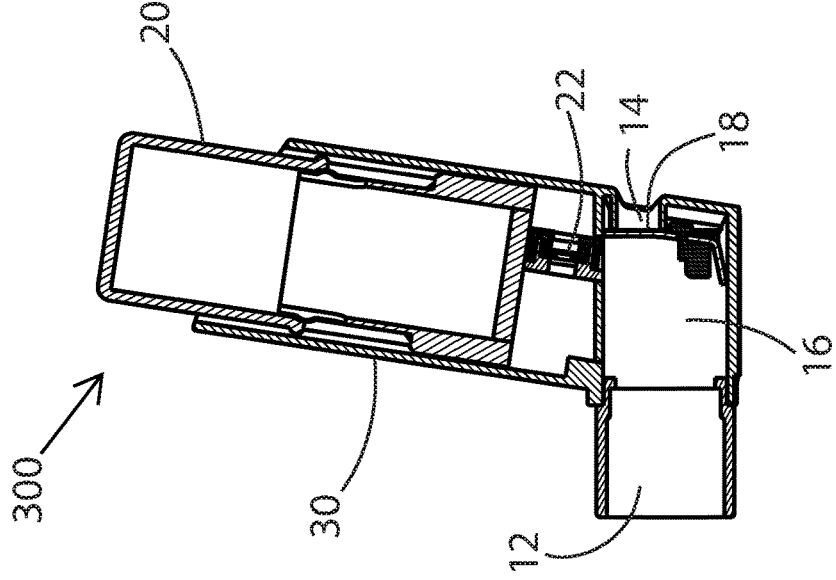

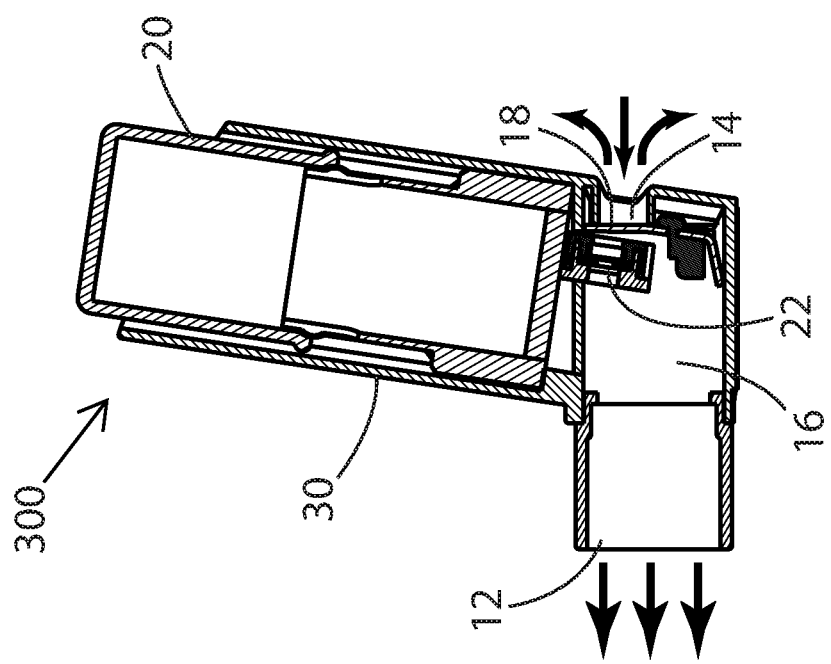

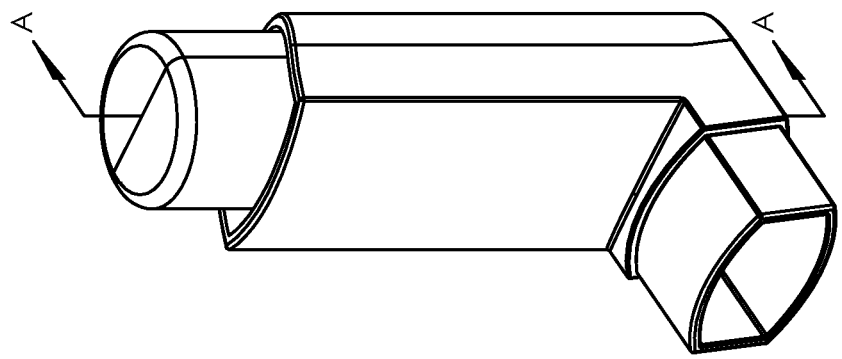

METERED DOSE INHALER TRAINING DEVICE

BACKGROUND

Respiratory inhalation devices are used to treat a number of different diseases and conditions, or to relieve symptoms associated therewith including asthma, chronic obstructive pulmonary disease (COPD), cystic fibrosis, among other illnesses. Use of respiratory inhaler devices can be complex and oftentimes difficult, as each type of device and/or each medication includes its own Instructions for Use (IFU). Some medications have numerous steps which must be followed in a precise manner in order to receive an accurate dosage of the medication. Moreover, some respiratory inhalation devices and medication require precise timing of multiple steps to be performed in conjunction with one another. Without proper training, these devices can be extremely difficult to use and can create a sense of anxiety in a user.

Self-management of chronic conditions can be complex and self-medication can often result in an unpleasant and/or ineffective experience. Experiences of patients that are new to drug delivery devices include anxiety, errors, and non-compliance. Drugs that are administered at home with devices account for over 200,000 adverse events in the Food and Drug Administration (FDA) Adverse Event Reporting System (AERS) database. The FDA considers patient errors as device failures. Consequently, the FDA is attentive and oftentimes critical of self-management devices. Device developers therefore, focus on ease of use of the device in development, but do not focus much attention to the ease of learning, which is the most relevant and most critical factor in reducing patient errors.

Asthma affects approximately 235 million people worldwide, a number estimated to grow to 400 million by 2025, with the highest growth in children. It is the most common chronic disease among children. In the US, 8.3% of the population (25 million people) has asthma. The prevalence of asthma in females is 29% higher than in males, According to the CDC (2009, USA only), asthma caused 8.9 million doctor visits, 1.9 million emergency room visits, 479,300 hospitalizations, and 3,400 deaths.

Asthma is commonly treated through therapies consisting of maintenance (control) and quick relief (rescue) medications. Maintenance medications are preventative and when used over time, can reduce airway inflammation and risks associated with asthma. Quick relief medications are reactive medications used to treat acute symptoms and dilate constricted airways. Proper medication and lifestyle management can limit the occurrence and severity of asthmatic episodes. Asthma plans, created by patients with their HCP, typically monitor lung performance and symptoms to adjust treatments and dosing as needed.

Chronic Obstructive Pulmonary Disease (COPD) is a progressive, lifelong disease characterized by poor airflow and lung performance Symptoms of COPD include coughing, shortness of breath, fatigue, frequent respiratory infections and wheezing. There are two main forms of COPD, chronic bronchitis is a disease in which the bronchi develop chronic inflammation and swelling due to the irregular growth of mucus glands and over time, progressive damage is caused to the intracellular walls of effected airways. Chronic bronchitis is the most common form of COPD, affecting approximately 12 million people in the USA. A second form of COPD is emphysema, wherein alveolar membranes deteriorate, reducing the surface area of the lung. Over time, emphysema reduces the elasticity and support of airways, leading to further complications such as collapsed lung and respiratory failure.

The primary cause of COPD is smoking. Secondary causes include air pollution, occupational exposures and genetics. COPD is currently the third leading cause of deaths in the United States (approximately 134,000 deaths annually). In the United States, there are approximately 13 million diagnosed cases of COPD and 24 million adults living with lung impairments, and there is currently no cure for COPD.

Cystic Fibrosis (CF) is an incurable chronic disease that affects the glands that produce mucus and sweat. A defective gene causes the body to produce unusually thick, sticky mucus that affects the lungs and digestive system. As the mucus builds up, it blocks airways in the lungs, which makes it increasingly difficult to breathe. Mucus buildup also encourages the growth of bacteria, which cause life-threatening lung infections. Mucus buildup also obstructs the pancreas from producing essential digestive enzymes. The intestines need these enzymes to process the nutrients in food, such as vitamins and minerals. People with CF also lose large amounts of salt when they sweat. This can cause an unhealthy imbalance of minerals in the blood. CF is one of the most common chronic lung diseases in children and young adults. About 30,000 children and adults in the United States (70,000 worldwide) have CF. Approximately 1,000 new cases of cystic fibrosis are diagnosed each year in the USA. More than 70% of patients are diagnosed with CF by age two. More than 45% of the CF patient population is age 18 or older.

Multi-sensory learning is very important for effectively learning new behaviors, particularly when there are multiple steps and requirements that must be met, such as with the use of self-medication devices. Additionally, it is critically important that these devices be used correctly to assure compliance and effective administration of medicaments to patents in need. Triggered by sensory stimulation, the brain constantly creates new network connections between neurons. Each time we learn, the new connections slightly change the brain. Multisensory learning is based on several neurophysiological and psychological principles, including: i) the human body has approximately 20 sensory systems, the sensory stimuli most relevant to learning are auditory, visual, somatosensory (tactile), gustatory, and olfactory; ii) multisensory learning engages multiple sensory modalities, which are interpreted in distinct areas of the brain; iii) sensory stimuli are integrated in the superior colliculus, the structure of the superior colliculus, located in the midbrain, contains a high proportion of multisensory neurons; iv) the more senses that are stimulated, the more network pathways are available for retrieval, thus, the better we learn. This is as long as each sense gets a signal at the same time, in the same space and with the same meaning; v) it is autonomous and ubiquitous, the brain is already wired for it and there are many instances of multisensory learning in everyday life; and vi) not only do the senses complement one another, they can modulate (strengthen) one another. This mutual reinforcement facilitates processing and retention in the brain.

There are numerous benefits of multisensory learning, some of which include: a) under the right conditions, information is processed and interpreted faster; b) better retention in memory and information is remembered over a longer period of time; c) distraction is avoided—if a sense (eye, ear, etc.) is not in use for learning, it will still be active, and if it receives a signal that is not in agreement with the subject matter, it all aspects of learning are interrupted; d) with multiple senses occupied, is easier to hold attention; e) a single sensory cue activates all areas of the brain that have received stimuli (cross-modal processing), this phenomenon is the most surprising and powerful discovery of the use of magnetic resonance imaging (MRI) in neuroscience, for example; and f) people who have entrenched neural pathways (older persons), multisensory learning is especially helpful in the acquisition of new knowledge that is contradictory to prior experience.

To take advantage of the neurological mechanisms in the brain, certain requirements need to be considered in regard to medicament training devices. The requirements for multisensory learning are: spatially, the sources of stimuli have to be in close proximity; temporally, the sources of stimuli have to be synchronous; semantically, the stimuli have to be congruous (see above); minimize sensory redundant information (both within mode and in between mode), otherwise, a split in attention will result. Additionally, active learning induces greater multisensory integration compared to passive observation. Active motor learning, where the learner engages in the real thing, modulates the establishment and processing of multisensory connections. Functional connectivity between visual and motor cortices is stronger after active learning than passive learning.

A four stage process often occurs in educating a new patient to use an unfamiliar drug delivery device. The first stage includes the training of sales representatives of a pharmaceutical company wherein the company has extensive control over the consistency of the training message. In the second stage, the sales representative trains the healthcare provider (HCP). Because both the sales representatives and healthcare providers are often stressed for time, and due to the enormous variance in training environments, message erosion can occur. The healthcare provider then trains the patient in the third stage. Typically, such a training session takes 30 minutes, a significant amount of time in a healthcare provider's day, and an amount of time the healthcare provider is often reluctant to give up. Because of the enormous variance in educational backgrounds and teaching experience of healthcare providers, significant message erosion is takes place in this four stage process. Lastly, the fourth stage includes a patient learning to use the device and practicing repeatedly with the device at home.

SUMMARY

In an embodiment, a metered dose inhaler (MDI) training device is provided herein. The MDI training device may include a housing having an inhalation port, an opening for receiving ambient air, the inhalation port and the opening are fluidly connected to provide an air flow channel, and a valve associated with the air flow channel, the valve having an opened state and a closed state, and an actuation member, wherein the valve is not allowed to enter the opened state if the actuation member is actuated prior to inhalation through the inhalation port.

In another embodiment, a metered dose inhaler (MDI) training device including a housing having an inhalation port and an opening for receiving ambient air is provided. The inhalation port and the opening are fluidly connected to provide an air flow channel An actuation member is provided, wherein if the actuation member is actuated prior to inhalation through the inhalation port, a portion of the actuation member blocks the opening, restricting airflow through the opening.

In still a further embodiment, a method for training a user to use a metered dose inhaler (MDI) in a correct sequence is provided, including obtaining an MDI training device having a housing including an inhalation port, an opening to receive ambient air, wherein the inhalation port and the opening are fluidly connected to provide an air flow channel, a valve associated with the air flow channel, the valve having an opened state and a closed state, and an actuation member at least partially receivable within the housing. The method further includes inhaling through the device via the inhalation port, and actuating the actuation member, wherein the valve is not allowed to enter the opened state if the actuation member is actuated prior to inhalation through the inhalation port, and wherein when inhalation occurs through the inhalation port during actuation of the actuation member, the valve is permitted to assume the opened state to allow air to pass through the opening and into the airflow channel.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 1 is a cross sectional view of an embodiment of a metered dose inhaler (MDI) training device taken at A-A of the perspective view of FIG. 9.

FIGS. 2A-2C are cross sectional views of the embodiment provided in FIG. 1 demonstrating correct stepwise use of the device.

FIG. 4 is a cross sectional view of another embodiment of an MDI training device FIGS. 5A-5C provide cross sectional views of the embodiment provided in FIG. 4 showing correct stepwise use of the device.

FIG. 7A is a cross sectional view of another embodiment of an MDI training device.

FIG. 7B-7C are cross sectional views of the embodiment of the MDI training device shown in FIG. 7A, demonstrating correct stepwise use of the device.

FIG. 7D is a cross sectional view of the embodiment of the MDI training device of FIG. 7A demonstrating incorrect stepwise use of the device.

FIG. 9 is a perspective view of an embodiment of an MDI training device.

DETAILED DESCRIPTION

Figure 3B:
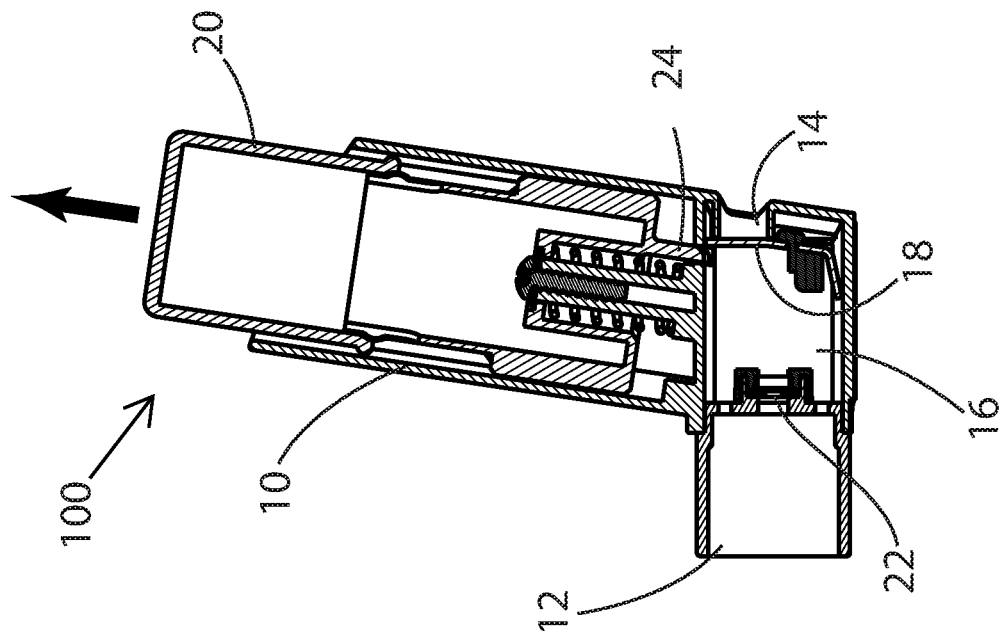
FIGS. 3A-B are cross sectional views of incorrect stepwise use of the device embodiment of FIG. 1 and FIGS. 2A-2C.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

Definitions

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context. It is to be noted that all ranges disclosed within this specification are inclusive and are independently combinable. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising."

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

The term "associated" or "association", as used herein, includes but is not limited to direct and indirect attachment, adjacent to, in contact with, partially or fully attached to, and/or in close proximity therewith. The term "value" as used herein, may refer to a specific value or a range of values.

The term "signal output component" as used herein may include sensory outputs provided to a user of the device, including but not limited to visual, audio, vibration or tactile (haptic) output, a flavor (gustatory output), a smellant or a fragrance, (olfactory output) among other possible sensory outputs. Signal outputs are used herein to communicate with and provide feedback to the user. In one non-limiting embodiment, the signal output component generates a visual output including at least one light or screen display (light emission diode, liquid crystal display) or a combination thereof. The visual output or feedback may include one or more visual outputs such as an LED and/or an LCD display, for example, which may be provided independently of one another or in combination with one another. The feedback may provide information to the user about the medicament device training. The LED or LCD may be activated by way of sensors, circuits, sounds, or the like.

In one non-limiting embodiment, a contact sensor, proximity sensor, pressure sensor, or flow rate sensor may cause activation of the LED or LCD, or may determine feedback provided to a user via audible, or other visual signal, in non-limiting embodiments by way of the signal output component. In a more particular embodiment, when the contact sensor detects contact or lack thereof between components of the MDI training device, feedback may be provided to the user. For example, a contact sensor disposed between the flange and the valve may indicate the incorrect sequence of steps were executed, i.e., the actuation member was actuated prior to inhalation through the inhalation port. In another non-limiting embodiment, a contact sensor may be provided to detect contact between the portion of the housing surrounding the opening and the valve to detect displacement of the valve relative to the opening to initiate feedback to the user. In alternative embodiments, if the MDI device is used in the incorrect sequence, or otherwise used incorrectly (i.e., less than predetermined flow rate during inhalation), no feedback may occur or a negative feedback may occur, whether it be by audible signal, visual signal, or other signal via the signal output component, In some non-limiting embodiments provided herein, the LCD screen(s) of the MDI training device may provide instructions to direct user in step by step use of the device by, for example, providing arrows pointing to the next step to be completed in the sequence, or by identifying errors during use of the device and/or displaying those errors in non-limiting embodiments.

In other non-limiting embodiments, feedback may be provided by way of a circuit. In one example, a closed circuit to open circuit, in some embodiments resulting from the closed to opened state of the valve, for example, may indicate to actuate the actuation member, which may include an LED, for example, which may provide a green light response via the LED once actuation member is actuated. If circuit remains closed, red LED may appear or be maintained, in one non-limiting example.

The term "opened state" as used herein refers to a state in which a valve is fully opened, allowing the air to pass through the opening. In some embodiments, in the opened state, when the air passes through the opening a signal output may be generated.

The term "closed state" as used herein refers to a state in which a valve is not fully opened. A valve in a closed state may block all airflow or may allow some air to pass through the opening less than in the opened state.

The term "fully opened" as used herein refers to a state in which a valve is sufficiently open to allow air to pass through to generate a signal output component. Examples of "fully opened" valve are shown in FIGS. 2A and 2B, in non-limiting examples.

The term "predetermined flow rate" as used herein refers to a flow rate greater than 0 Liters per minute (L/m). In some non-limiting embodiments, the predetermined flow rate may include a range between 0 and 40 L/m, and in other non-limiting embodiments, the predetermined flow rate may include a range between 25-35 L/m.

The use of a respiratory inhaler requires precise coordination of events to receive a proper dosage of a medicament. Practice using an inhaler can assist a patient in establishing autonomous time and/or motor skills. Only frequent use of the inhaler can improve timing and provide a user with the tools to develop the technique to use the inhaler drug delivery device to receive a required dose of medicament. Benefits of the respiratory training device embodiments described herein include familiarizing patients with the training device, which closely resembles a drug delivery device on the market so as to increase patient confidence and comfort in using the device. This will assist in reducing patient error in using the device, allow a user to develop autonomous motor skills and reduce the amount of time of and reduce the burden on health care providers to assist and train patients to use the device.

Two primary settings for training a user to use a respiratory inhaler drug delivery device with the use of the respiratory inhaler training device are generally found. The first setting is in a healthcare provider's office or other healthcare setting in which a physician or a nurse most likely educates themselves on how to use the respiratory inhaler training device. The healthcare provider will then use the training device to train the patient in a typical exam room setting. The second setting is an at-home setting, wherein the patient will practice with the training device at home, either alone or in most instances, with a non-medically trained companion. The training device will be used, therefore, without medical supervision before the first use of the drug delivery respiratory inhaler device. A refresher training with the training device may occur as needed just before the subsequent use of the drug delivery respiratory inhaler device.

The Food and Drug Administration (FDA) mandates that all users of medical devices used in home healthcare have readable and understandable instructions in order to operate these devices safely and effectively. These instructions can be wordy and can sometimes cause confusion for users of the device. Embodiments of a training device provided herein for use as a respiratory inhaler training device provide an ability to identify mistakes in the use of a respiratory inhaler delivery device before the drug delivery device is used by a patient, increase compliance in proper use of the drug delivery device, improve adequacy of use of the drug delivery device, identify errors patients make with the device, intervene where a patient makes a mistake, and guide the patient through proper use of the device.

The training experience allows a patient to establish muscle memory. Some of the events simulated include: 1) inhalation, 2) activating the actuation member by depression, for example, wherein inhalation must occur before activation of the actuation member 3) providing a signal to prompt a user when to perform a step (i.e., activating the actuation member), wherein an audio, visual, or haptic output may be used, and 5) providing a signal to a user when an incorrect step is performed (or providing no signal to the user to indicate an error has occurred), or when an out of sequence step is performed via audio, visual, or haptic output, for example.

Turning to the Figures, FIG. 1 and FIGS. 2A-2C provide cross sectional views of a metered dose inhaler (MDI) training device embodiment 100, including a housing 10 having an inhalation port 12, an opening 14 for receiving ambient air, for example, wherein the inhalation port 12 and the opening 14 are fluidly connected to provide an air flow channel 16, and a valve 18 associated with the air flow channel 16. The valve 18 may include an opened state and a closed state. An actuation member 20 is also provided and may be movable relative to the housing 10, wherein the valve 18 is not allowed to enter the opened state if the actuation member 20 is actuated prior to inhalation through the inhalation port 12. In a non-limiting embodiment, the actuation member 20 may include a button, toggle, or other device known to those skilled in the art to actuate such a device. In another non-limiting embodiment, the actuation member 20 may include at least part of a canister receivable within at least a portion of a housing 10, or at least associated with the housing 10. The canister may, for example, include medicament or may be void of medicament in non-limiting embodiments. The embodiment 100 shown in FIG. 1 and FIGS. 2A-2C also shows a whistle 22 disposed in the airflow channel 16. In a non-limiting embodiment, the whistle may be disposed between the opening and the inhalation port as shown. A flange 24 is also shown in association with the actuation member 20, directly or indirectly, such that movement of the actuation member 20 relative to the housing 10 in a first direction causes the flange 24 to move in the first direction. Release of the actuation member 20, in a non-limiting embodiment, allows the actuation member 20 to move in a second direction relative to the housing 10. Consequently, in some non-limiting embodiments, when the actuation member 20 is released, the flange 24 moves in the second direction relative to the housing 10. In another non-limiting embodiment, the flange 24 may be associated with the housing 10. The flange 24 may still be associated with the actuation member 20, for example FIGS. 2A-2C are cross sectional views showing the step-by-step use of the embodiment of the device 100 in FIG. 1 wherein when the actuation member 20 is actuated during inhalation through the inhalation port 12, the valve 18 is permitted to assume the opened state to allow air to pass through the opening 14 and the inhalation port 12. In FIG. 2A, the arrows labeled "1" identify a first step of inhalation by a user through the inhalation port 12, wherein air enters the device via the opening 14 marked by the arrows labeled as "2" such that valve 18 is moved away from the opening 14 under the pressure of the air being inhaled into the device 10, and consequently, air passes through the whistle 22 to sound the whistle 22 to provide feedback of correct order of operation and correct inhalation using the device 100. As shown, when the air traverses the whistle at a predetermined flow rate, the whistle produces an audible signal, providing a feedback to a user. In FIG. 2B, once the whistle 22 has sounded, the actuation member 20 can be depressed as shown by step "4", causing the flange 24 to move in a first direction relative to the housing 10 allowing the whistle 22 to remain open, such that the feedback produced by the whistle 22 will continue to sound during this step. In some non-limiting embodiments, actuation by movement of the actuation member 20 in a first direction relative to the housing 10 may cause the flange 24 to press against the open valve 18 to further bias it away from the opening 14 and further sound the whistle 22. Once the actuation member 20 is released as shown in FIG. 2C, the actuation member 20 moves in a second direction relative to the housing 10 and returns to its pre-actuation position, allowing the valve 18 to return to its position over the opening 14, identified by step "5" in FIG. 2C. FIGS. 2A-C show correct sequential use of the device embodiment 100. As shown in FIGS. 2A-C, in a non limiting embodiment, the valve 18 may include a deflectable flap. In an alternative embodiment, the valve 18 may include a hinged door component and a biasing member, wherein the hinged door component rotates against the biasing member when the valve assumes the opened state.

Figure 3A:
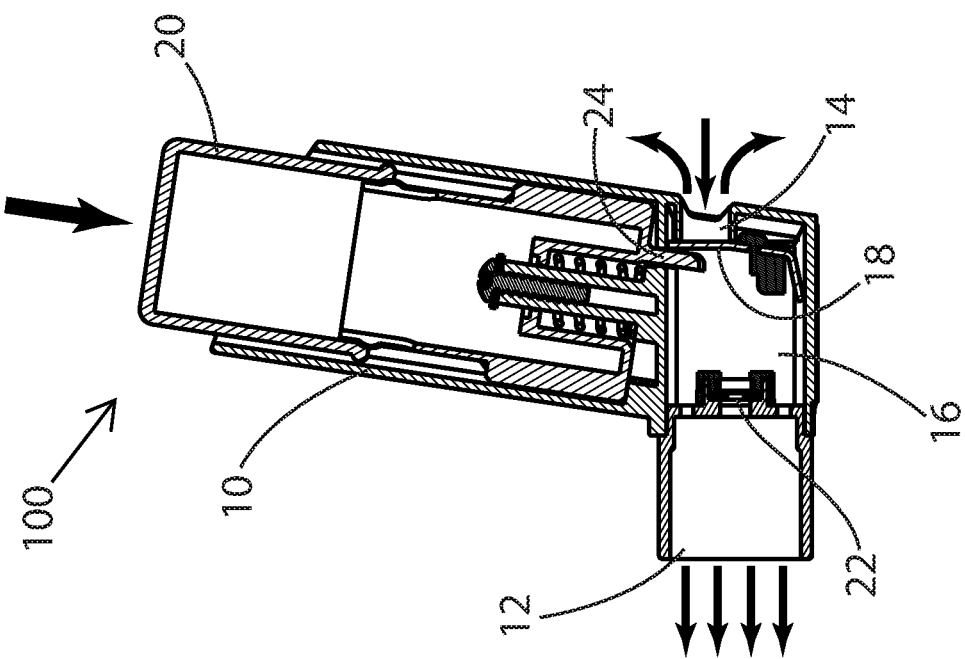

An incorrect sequential use of the device 100 is shown in FIGS. 3A-3B. Initiation of actuation of the actuation member 20 (step 1) prior to inhalation via the inhalation port 12 (step 2) causes the flange 24 to abut the valve 18 to maintain the valve 18 in the closed state.

In a further, non-limiting embodiment, the actuation member 20 may include a canister, and the canister, or a portion thereof, may but the valve 18 when the actuation member 20 is actuated to maintain the valve 18 in the closed state if the actuation member 20 is actuated prior to inhalation through the inhalation port 12.

In one embodiment, the valve 18 may include a septum material. In another embodiment, a visual output component may be provided in association with the device embodiment 200, as shown in FIG. 4. FIG. 4 provides an embodiment 200 in which a light emission diode (LED) 26 is provided as a non-limiting example of a visual output component. Other embodiments may include liquid crystal display (LCD), other lights or textual visual outputs in addition to or in place of the LED 26 shown in FIG. 4. One or more visual output components may be associated with the device embodiment 200. The visual output components may be associated with the housing 10 or with the actuation member 20, or both, in some non-limiting embodiments.

FIGS. 5A-5C show the embodiment of the device 200 provide din FIG. 4, and indicate the correct sequence of steps of use of the device beginning with inhalation through the inhalation port 12 (step 1), causing air to enter the device via the opening 18 (step 2) and to pass through the opened valve 18, and through the signal output component, in this example, the whistle 22 (step 3), followed by initiation of the visual output component 26 (step 4) by, for example, lighting of the LED or lighting the LED in a green color on the housing 10 indicating the steps were performed in the correct sequence to provide feedback to a user, for example. Furthermore, a visual output component of the actuation member 20 may occur in addition to, or in place of the activation of a visual output component 26 on the housing 10 to indicate the next step in the sequence to actuate the actuation member 20 (step 5). Release of the actuation member 20 and return to its original position is shown in FIG. 5C after use of the device 200. In one non-limiting embodiment, the LED may be provided as a patterned, or blinking, LED until a step is correctly performed in the use of the device, wherein following that step being performed correctly, the blinking (or patterned) LED may change to a solid LED output in a predetermined color.

In some non-limiting embodiments, the visual output component may include one or more LEDs on the actuation member 20, wherein the actuation member LEDs are activated to output a first predetermined LED pattern and/or a first predetermined LED color. The first predetermined LED pattern may include a flashing pattern of LED light. Upon actuating the actuation member 20, the LEDs are activated to provide a non-patterned LED output, in another embodiment.

Figure 6B:
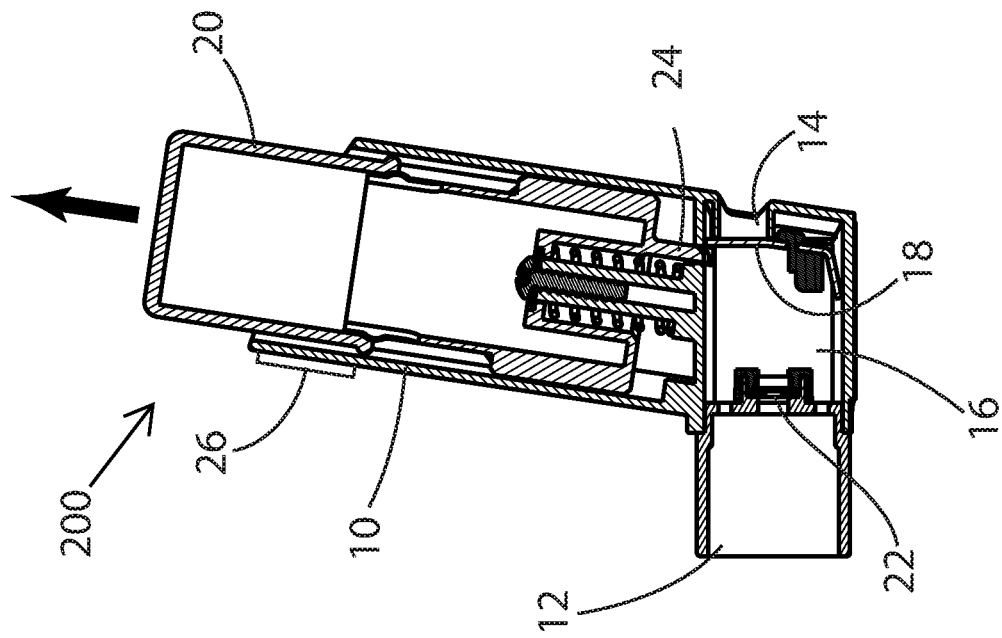
FIGS. 6A-6B provide incorrect stepwise use of the embodiment of the device provided in FIG. 4 and FIGS. 5A-5C.
Figure 6A:
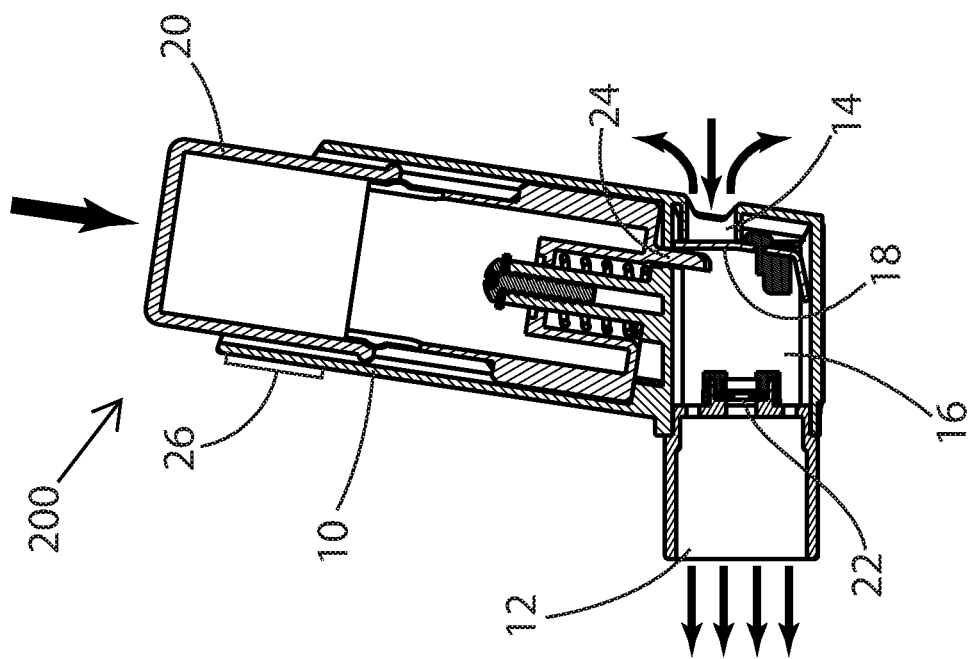

FIGS. 6A-6B show an example of the use of the device 200 shown in FIGS. 4 and 5A-C in an incorrect sequence, wherein in one example, actuation of the actuation member 20 (step 1 as shown) before inhalation via the inhalation port 14 (step 3 as shown) blocks the opening 14 preventing the valve 18 from allowing air to enter through the opening 14 into the airflow channel 16, such that air fails to traverse the whistle 22 at a predetermined flow rate and the whistle 22 fails to produce an audible signal, or in another embodiment, produces an audible signal that is different from the audible signal produced when sufficient air is allowed to enter the airflow channel 16 when the correct sequence of steps is performed with the device 200, resulting in a negative feedback to the user. The actuation member 20 may include a button, or other type of device actuatable by a user and known to those skilled in the art to which the invention pertains. In another non-limiting embodiment, the actuation member 20 may include a canister, the canister being receivable within the housing 10, and being compressible or moveable relative to the housing, for example, upon actuation of the canister (i.e., the actuation member 20) to activate the device.

In this embodiment, if the steps are performed in the incorrect sequence as shown in FIGS. 6A-B, in a non-limiting embodiment, the visual output component 26 may provide a red colored LED light to a user indicating the steps have been performed out of sequence, for example, or there may be no visual output provided via the visual output component in another non-limiting embodiment.

In yet another embodiment 300 shown in FIGS. 7A-D, a device housing 30 including an actuation member 20 is provided, the device having an inhalation port 12, an opening 14 for receiving ambient air, and a valve 18 is provided. An airflow channel 16 is provided between the inhalation port 12 and the opening 14. In this embodiment, the signal output component (i.e., the whistle 22, for example) may be associated with the actuation member 20 and may be movable relative to the airflow channel 16 upon actuation of the actuation member 20. For example, in one non-limiting embodiment, positive feedback to a user may only occur upon actuation of all of the steps required for actuation of the device 300, in the correct sequence. For example, as shown in FIG. 7B, inhalation via the inhalation port 12 during actuation of the actuation member 20, whereupon the valve 18 allows ambient air to traverse the opening 14 and pass through into the airflow channel 16, followed by actuation of the actuation member 20 provides feedback to the user, i.e., by activating the signal output component 22, for example. In this embodiment, the signal output component includes a whistle 22, which will not sound until it enters the airflow channel 16 which occurs upon actuation of the actuation member 20 while the valve 18 is in the opened state as shown in FIG. 7B-7C.

In another non-limiting embodiment, actuation of the actuation member 20 during inhalation via the inhalation port 12 of the embodiment 300 of the device may cause a portion of the actuation member 20 or the signal output component 22, in a non-limiting embodiment, to press against the valve and further open the valve 18 to allow more air to enter the airflow channel 16 via the opening 14 as shown in FIG. 7B-7C.

If the actuation member 20 is actuated prior to inhalation via the inhalation port 12 or once inhalation via the inhalation port 12 has stopped, the valve 18 remains in or returns to a closed state as shown in FIG. 7D, the valve 18 associates with the opening 14, and air is prevented from flowing into the airflow channel 16 via the opening 18 preventing activation of the signal output component, i.e., the whistle 22.

Figure 8:
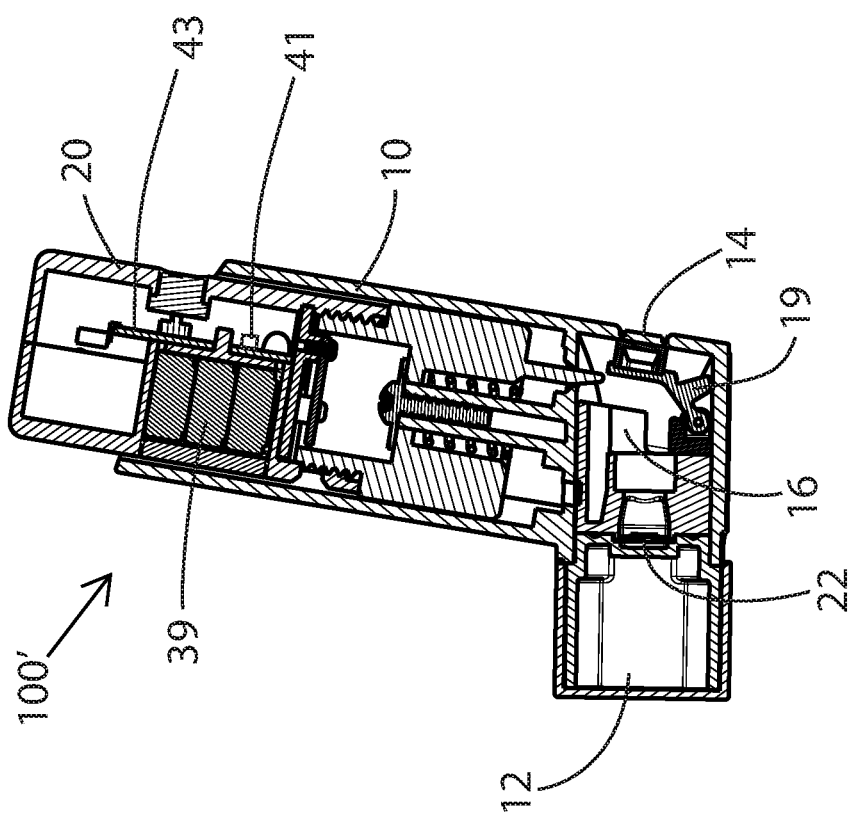
FIG. 8 is a cross sectional view of another embodiment of the MDI training device.

FIG. 8 is a cross sectional view of another embodiment 100' of the MDI training device including a housing 10 having an inhalation port 12, an opening 14 for receiving ambient air, and a whistle or other signal output component 22, in a non-limiting embodiment, in an airflow channel 16. An actuation member 20 is also provided, and is movable relative to the housing 10. A valve 19 is associated with the air flow channel, the valve having an opened state and a closed state, wherein the valve 19 is not allowed to enter the opened state if the actuation member 20 is actuated prior to inhalation through the inhalation port 12. As shown in FIG. 8, the valve 19 may include a hinged door component that rotates between an opened state and a closed state. In a non-limiting embodiment, the valve may include a hinged door component and/or a biasing member. In one embodiment, the valve may include a hinged door component and a biasing member, wherein the hinged door component rotates against the biasing member in a first direction when the valve assumes the opened state, and rotates about the biasing member in a second direction when the valve assumes the closed state. The embodiment 100' shown in FIG. 8 also includes a power source 39, which may include a battery in one or more non-limiting embodiments, a microphone 41, and a processor 43, for example.

The power source 39 may be used to power any of the components of the device, in one non-limiting embodiment, which may include the signal output component, visual output component, the processor, or the microphone, for example.

FIG. 9 includes a perspective view of an embodiment of a MDI training device, wherein a cross sectional axis A-A is indicated thereon.

In another embodiment herein, a method for training a user to use a metered dose inhaler (MDI) in a correct sequence is provided. The method includes obtaining an MDI training device having a housing including an inhalation port, an opening to receive ambient air, wherein the inhalation port and the opening are fluidly connected to provide an air flow channel, a valve associated with the air flow channel, the valve having an opened state and a closed state, and an actuation member at least partially receivable within the housing. The method further includes inhaling through the device via the inhalation port, and actuating the actuation member wherein the valve is not allowed to enter the opened state if the actuation member is actuated prior to inhalation through the inhalation port, and wherein when inhalation occurs through the inhalation port prior to actuation of the actuation member, the valve is permitted to assume the opened state to allow air to pass through the opening and the inhalation port. In a further embodiment, when inhalation occurs through the inhalation port prior to actuation of the actuation member, a positive feedback is provided to the user.

In still a further embodiment, the method is provided wherein a whistle is in the airflow channel, wherein when inhalation occurs through the inhalation port prior to actuation of the actuation member, an audible signal is provided to the user. When actuation of the actuation member occurs prior to inhalation through the inhalation port, a negative feedback is provided to the user. In one non-limiting embodiment, the negative feedback comprises no audible signal provided to the user. In another non-limiting embodiment, the negative feedback comprises an audible signal in a predetermined range. In one embodiment, the audible signal is provided to the user via the whistle when the inhalation occurs at a predetermined flow rate. In another non-limiting embodiment, the whistle may be movable into the airflow channel by actuation of the actuation member.

In non-limiting embodiments herein, positive or negative feedback may be provided by audible, visual, gustatory, or haptic feedback to a user, or a combination thereof. There are various ways in which the embodiments herein may provide feedback to a user. For example, feedback may be provided, or in a particular example, visual or audible signal output to a user may be accomplished in a number of ways. In one non-limiting embodiment, the actuation of the actuation member may be identified with a microphone in the device such that once an audible indication that the actuation member has been actuated is identified by the microphone, an LED may be activated to provide visual feedback to a user. Furthermore, in embodiments in which an audible feedback is provided to a user to indicate that inhalation has occurred, for example, when a whistle is sounded upon correct inhalation prior to actuation of the actuation member, this audible feedback can be picked up by the microphone 41 and translated into visual feedback via the visual output component. The information may be processed via a processor 43 associated with the device which may determine the particular visual output or other signal output to provide to a user based on the signals and/or sounds received during use of the device, in one non-limiting embodiment. For example, the processor 43 may determine a certain LED pattern to output to a user when a step, or sequence of steps, have been correctly performed.

In some non-limiting embodiments, information may be sent to and from the MDI training device to another device or external source. For example, information about a training or a sequence of trainings with the MDI training device may be transmitted to a physician, or a family member, or may be stored on the MDI training device itself. This information may be used to identify errors in use of the device and also correct use of the device. The information may be useful to facilitate further trainings with the MDI training device, or to recommend a consultation with a medical professional about a use of the device.

In some non-limiting embodiments provided herein, the whistle only provides a sound once a predetermined flow rate is achieved. In other non-limiting embodiments, the whistle provides a sound to a user at any flow rate of inhalation; however, at the predetermined flow rate, a certain identifiable whistle is produced. For example, at flow rates not within the predetermined flow rate, the whistle may produce a lower tone, and at flow rates within the predetermined flow rate, the whistle may produce a higher tone to differentiate between correct and incorrect inhalation. Feedback may be provided in a number of different ways with different sounds, different tones produced by the whistle or other signal output components described herein such as sounds provided via a speaker. In other non-limiting embodiments, feedback may be provided by an absence of sound, visual, haptic, gustatory, or other output via the signal output component.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the preceding definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Accordingly, it is intended that the invention be limited only by the spirit and scope of the appended claims. The teachings of all references cited herein are incorporated in their entirety to the extent not inconsistent with the teachings herein.

What is claimed herein is:

1. A metered dose inhaler (MDI) training device, comprising:
    a housing comprising an inhalation port, an opening for receiving ambient air, the inhalation port and the opening are fluidly connected to provide an air flow channel, and a valve associated with the air flow channel, the valve having an opened state and a closed state, and an actuation member, wherein the valve is not allowed to enter the opened state if the actuation member is actuated prior to inhalation through the inhalation port.

2. The MDI training device of claim 1, wherein when the actuation member is actuated following initiation of inhalation through the inhalation port, the valve is permitted to assume the opened state to allow air to pass through the opening and the inhalation port.

3. The MDI training device of claim 2, further comprising a whistle disposed between the opening and the inhalation port, wherein the ambient air traverses the whistle during an inhalation when the valve in the opened state, such that when the air traverses the whistle at a predetermined flow rate, the whistle produces an audible signal, providing a feedback to a user.

4. The MDI training device of claim 1, wherein the valve comprises a deflectable flap.

5. The MDI training device of claim 2, wherein the valve comprises a hinged door component and a biasing member, wherein the hinged door component rotates against the biasing member when the valve assumes the opened state.

6. The MDI training device of claim 1, wherein a flange is associated with the actuation member, the flange abuts the valve, and the valve remains in the closed state if the actuation member is actuated prior to inhalation through the inhalation port.

7. The MDI training device of claim 1, wherein the actuation member comprises a canister, wherein at least a portion of the canister abuts the valve to maintain the valve in the closed state if the actuation member is actuated prior to inhalation through the inhalation port.

8. The MDI training device of claim 1, wherein the valve comprises a septum material.

9. The MDI training device of claim 1 further comprising a signal output component.

10. The MDI training device of claim 9, wherein the signal output component comprises a visual output component comprising one or more light emitting diodes (LEDs).

11. The MDI training device of claim 10, wherein one or more LEDs are disposed on the actuation member.

12. The MDI training device of claim 11, wherein upon inhalation through the inhalation port during actuation of the actuation member, the actuation member LEDs are activated to output a first predetermined LED pattern and/or a first predetermined LED color.

13. A metered dose inhaler (MDI) training device comprising:
    a housing comprising an inhalation port and an opening for receiving ambient air, the inhalation port and the opening are fluidly connected to provide an air flow channel, and
    an actuation member, wherein if the actuation member is actuated prior to inhalation through the inhalation port, a portion of the actuation member blocks the opening, restricting airflow through the opening.

14. The MDI training device of claim 13, wherein when the actuation member is actuated during inhalation through the inhalation port, ambient air is permitted enter the housing through the opening.

15. The MDI training device of claim 14 further comprising a whistle disposed between the opening and the inhalation port, wherein when the ambient air traverses the whistle during an inhalation at a predetermined flow rate, the whistle produces an audible signal, providing a feedback to a user, and wherein when the actuation member is actuated prior to inhalation through the inhalation port, the air fails to traverse the whistle at a predetermined flow rate and the whistle fails to produce an audible signal providing a feedback to a user.

16. The MDI training device of claim 13, further comprising a signal output component.

17. The MDI training device of claim 16, wherein the signal output component comprises a visual output component, comprising one or more light emitting diodes (LEDs).

18. The MDI training device of claim 17, wherein one or more LEDs are disposed on the actuation member.

19. A metered dose inhaler (MDI) training device, comprising:
    a housing comprising an inhalation port and an opening for receiving ambient air, wherein the inhalation port and the opening are fluidly connected to provide an airflow channel, and a valve associated with the opening, the valve having an opened state and a closed state, and
    an actuation member having a flange associated therewith;
    such that inhalation through the inhalation port during actuation of the actuation member causes the valve to enter the opened state, and air to enter the airflow channel through the opening, and wherein when the actuation member is actuated prior to inhalation through the inhalation port, the flange interacts with the valve in the closed state, to prevent the valve from entering the opened state.

\* \* \* \* \*